United States Patent
Dong et al.

(10) Patent No.: US 10,709,647 B2
(45) Date of Patent: Jul. 14, 2020

(54) SKIN CARE COMPOSITION COMPRISING TURBOSTRATIC BORON NITRIDE

(71) Applicant: Conopco, Inc., Englewood Cliffs, NJ (US)

(72) Inventors: Wenyan Dong, Shanghai (CN); Naresh Dhirajlal Ghatlia, Bangalore (IN); Lin Wang, Shanghai (CN); Shuqi Zhu, Shanghai (CN)

(73) Assignee: Conopco, Inc., Englewood Cliffs, NJ (US)

( * ) Notice: Subject to any disclaimer, the term of this patent is extended or adjusted under 35 U.S.C. 154(b) by 281 days.

(21) Appl. No.: 15/769,910

(22) PCT Filed: Sep. 22, 2016

(86) PCT No.: PCT/EP2016/072573
§ 371 (c)(1),
(2) Date: Apr. 20, 2018

(87) PCT Pub. No.: WO2017/071886
PCT Pub. Date: May 4, 2017

(65) Prior Publication Data
US 2018/0311126 A1    Nov. 1, 2018

(30) Foreign Application Priority Data

Oct. 27, 2015  (WO) ............... PCT/CN2015/092931
Dec. 2, 2015   (EP) .................................. 15197451

(51) Int. Cl.
| | |
|---|---|
| *A61K 8/25* | (2006.01) |
| *A61K 8/29* | (2006.01) |
| *A61Q 1/02* | (2006.01) |
| *A61K 8/895* | (2006.01) |
| *A61K 8/02* | (2006.01) |
| *A61K 8/06* | (2006.01) |
| *A61K 8/19* | (2006.01) |
| *A61K 8/27* | (2006.01) |
| *A61Q 19/08* | (2006.01) |

(52) U.S. Cl.
CPC .............. *A61K 8/25* (2013.01); *A61K 8/0279* (2013.01); *A61K 8/062* (2013.01); *A61K 8/19* (2013.01); *A61K 8/27* (2013.01); *A61K 8/29* (2013.01); *A61K 8/895* (2013.01); *A61Q 1/02* (2013.01); *A61Q 19/08* (2013.01)

(58) Field of Classification Search
CPC . A61K 8/19; A61K 8/25; A61Q 19/08; A61Q 1/02
See application file for complete search history.

(56) References Cited

U.S. PATENT DOCUMENTS

| | | |
|---|---|---|
| 5,283,062 A | 2/1994 | Elliott et al. |
| 2005/0002976 A1 | 1/2005 | Wu |
| 2005/0041373 A1 | 2/2005 | Pruss et al. |
| 2007/0054122 A1 | 3/2007 | Paisner et al. |
| 2007/0207102 A1 | 9/2007 | Student et al. |
| 2012/0058342 A1 | 3/2012 | Lodyga et al. |
| 2012/0114905 A1 | 5/2012 | Engler et al. |
| 2013/0011317 A1 | 1/2013 | Prilutsky et al. |
| 2014/0335136 A1 | 11/2014 | Brieva et al. |

FOREIGN PATENT DOCUMENTS

| | | |
|---|---|---|
| EP | 1769786 | 2/2010 |
| EP | 2749264 | 7/2014 |
| EP | 2902360 | 8/2015 |
| FR | 2968545 | 5/2013 |
| FR | 2992197 | 12/2013 |
| WO | WO2008075282 | 6/2008 |
| WO | WO2009038712 | 3/2009 |
| WO | WO2012027194 | 3/2012 |
| WO | WO2013190114 | 12/2013 |
| WO | WO2013190709 | 12/2013 |
| WO | WO2014097972 | 6/2014 |
| WO | WO2014111833 | 7/2014 |

OTHER PUBLICATIONS

Momentive Softouch CC6058, Momentive Inventing Possibilities Technical Data Sheet, 2011, pp. 1-4; XP55277007,.
Momentive Softouch CC6097, Momentive Inventing Possibilities Technical Data Sheet, 2015, pp. 1-3; XP55325616, ., US.
IPRP2 in PCTEP2016072573, Sep. 8, 2017.
Search Report and Written Opinion in EP15197451, dated Jun. 13, 2016.
Search Report and Written Opinion in PCTEP2016072573, dated Dec. 13, 2016.

*Primary Examiner* — Kortney L. Klinkel
(74) *Attorney, Agent, or Firm* — Ellen Plotkin

(57) ABSTRACT

Disclosed is a personal care composition comprising turbostratic boron nitride, porous silica having a specific surface area of higher than 300 m²/g, and a cosmetically acceptable carrier.

15 Claims, No Drawings

SKIN CARE COMPOSITION COMPRISING TURBOSTRATIC BORON NITRIDE

FIELD OF THE INVENTION

The present invention relates to a personal care composition. In particular, the personal care composition comprises turbostratic boron nitride and porous silica.

BACKGROUND OF THE INVENTION

Ageing brings with it many changes to the appearance of skin. Of particular concern to individuals wishing to maintain a youthful appearance is the reduction or elimination of skin imperfections such as wrinkles, age spots or general unevenness of skin tone.

Thus there has been considerable effort by the cosmetics industry to provide compositions which can mask or at least attenuate skin imperfections. Often this is achieved by creation of a matte effect using materials such as talc, silica, kaolin and other inorganic particulates. These inorganic particulates achieve a matte effect due to their optical properties.

An alternative approach is referred to as achieving blurring effect. Here the incoming light is distorted by scattering (lensing). Components of the cosmetic composition in this mechanism operate as lenses to bend and twist light in a variety of directions.

Traditional approaches, unfortunately, either hide imperfections in the absence of radiance or result in radiance and healthy glow but with aesthetically displeasing skin appearance, for example, through enhanced visibility of skin topography.

We have recognised that there remains a need to provide a compositions which are capable of giving better blurring effect to skin, while maintaining preferably improving lightness. Therefore, after extensive experimentation, we developed a personal care composition comprising turbostratic boron nitride, porous silica and a cosmetically acceptable carrier, which has a higher blurring efficacy without compromise of lightness.

SUMMARY OF THE INVENTION

In a first aspect, the present invention provides a personal care composition comprising turbostratic boron nitride, porous silica having a specific surface area of higher than 300 $m^2/g$, and a cosmetically acceptable carrier.

In a second aspect, the present invention provides a method of reducing the appearance of fine lines, wrinkles, pores and/or blemish spots; evening skin tone, or a combination thereof on skin comprising the step of applying a composition of the present invention on the desired skin surface.

In a third aspect, the present invention provides use of composition of the present invention for reducing the appearance of fine lines, wrinkles, pores and/or blemish spots; evening skin tone, or a combination thereof on the desired skin surface.

All other aspects of the present invention will more readily become apparent upon considering the detailed description and examples which follow.

DETAILED DESCRIPTION OF THE INVENTION

Except in the examples, or where otherwise explicitly indicated, all numbers in this description indicating amounts of material or conditions of reaction, physical properties of materials and/or use may optionally be understood as modified by the word "about".

All amounts are by weight of the composition, unless otherwise specified.

It should be noted that in specifying any range of values, any particular upper value can be associated with any particular lower value.

For the avoidance of doubt, the word "comprising" is intended to mean "including" but not necessarily "consisting of" or "composed of". In other words, the listed steps or options need not be exhaustive.

The disclosure of the invention as found herein is to be considered to cover all embodiments as found in the claims as being multiply dependent upon each other irrespective of the fact that claims may be found without multiple dependency or redundancy.

"Turbostratic boron nitride (t-BN)" as used herein refers to boron nitride having oxygen impurity in the boron nitride crystal lattice.

"Silicone elastomer" as used herein refers to deformable organopolysiloxane with viscoelastic properties.

"Specific surface area" as used herein refers to specific surface area determined according to Brunauer-Emmett-Teller method. The value of the specific surface area was measured by meeting the requirements set out in ASTM standard D 3663-78.

"Diameter" as used herein refers to particle diameter in non-aggregated state unless otherwise stated. For polydisperse samples having particulate with diameter no greater than 1 μm, diameter means the z-average diameter measured, for example, using dynamic light scattering (see international standard ISO 13321) with an instrument such as a Zetasizer Nano™ (Malvern Instruments Ltd, UK) unless otherwise stated. For polydisperse samples having particulate with diameter no less than 1 μm, diameter means the apparent volume median diameter (D50, also known as ×50 or sometimes d(0.5)) of the particles measurable for example, by laser diffraction using a system (such as a Mastersizer™ 2000 available from Malvern Instruments Ltd) meeting the requirements set out in ISO 13320 unless otherwise stated.

Typically, the turbostratic boron nitride has an average diameter in the range of 200 nm to 100 microns, more preferably 500 nm to 50 microns, even more preferably from 1 to 15 microns, still even more preferably from 3 to 12 microns and most preferably from 4 to 9 microns.

The specific surface area of the turbostratic boron nitride is preferably from 5 to 80 $m^2/g$, more preferably from 10 to 60 $m^2/g$ and even more preferably from 15 to 40 $m^2/g$. As per especially preferred aspects, the specific surface area of the turbostratic boron nitride is at least 10 $m^2/g$, more preferably at least 20 $m^2/g$, further more preferably at least 25 $m^2/g$.

The content of oxygen in the turbostratic boron nitride is preferably at least 0.2% by mole of the turbostratic boron nitride, more preferably from 0.5 to 3%, even more preferably from 1 to 2%, and most preferably from 1.2 to 1.8% by mole of the turbostratic boron nitride.

The turbostratic boron nitride used in the present invention typically has a tap density ranging from 0.1 $g/cm^3$ to 1 $g/cm^3$ and more preferably from 0.2 $g/cm^3$ to 0.6 $g/cm^3$. Tap density, as used herein, refers to a measure of the density of a powder. The value of tap density refers to the values measured in conformity with international standard ISO 787-11.

Particularly preferred turbostratic boron nitride is Softouch* Boron Nitride Powder CC6097 from Momentive.

For sake of better blurring, and/or gloss of the skin, the turbostratic boron nitride is preferably present in amount of 0.01 to 15% by weight of the composition, more preferably 0.1 to 12%, even more preferably from 0.4 to 8%, still even more preferably from 1 to 5% and most preferably from 2 to 4% by weight of the composition.

The porous silica is preferably non-fumed silica. Preferably, the porous silica is hydrophilic. Even more preferably the porous silica is unmodified porous silica microsphere. Hydrophilic porous silica as used herein refers to silica having a water absorption value of greater than 10 g of water/100 g of particle measured in same manner as described in ASTM Method D281-84 but using water instead of oil. Microsphere refers to spherical particle having average diameter of 0.5 to 50 microns, more preferably from 1 to 15 microns.

The specific surface area of the porous silica is preferably at least 350 $m^2/g$, more preferably from 400 to 1000 $m^2/g$, even more preferably from 550 to 880 $m^2/g$ and most preferably from 590 to 810 $m^2/g$.

The porous silica has the capability of absorbing large amounts of oils. Preferably, the porous silica is a porous silica microsphere having an oil absorption value of higher than 100 g/100 g, more preferably higher than 200 g/100 g and even more preferably higher than 280 g/100 g. The oil absorption value refers to the values measured in conformity with ASTM Method D281-84.

The porous silica preferably has an average diameter of 200 nm to 40 microns, more preferably from 0.6 to 25 microns, even more preferably from 1 to 20 microns, still even more preferably from 1.5 to 12 microns and most preferably from 2 to 5 microns. To have a better sensory, the porous silica is preferably substantially uniform in size which means less than 5% of the porous silica have a diameter less than 0.5 times the average diameter and less than 5% of the porous silica have a diameter greater than 1.5 times the average diameter. In another aspect, the range of the diameter of the porous silica is preferably 0.8 to 1.2 times the average diameter, more preferably 0.9 to 1.1 times the average diameter.

Particularly preferred porous silica includes MSS-500/3H, MSS-500/H from Kobo Products Inc.

The porous silica is preferably present in amount of 0.01 to 20% by weight of the composition, more preferably from 0.05 to 14%, even more preferably from 0.2 to 9%, still even more preferably from 0.4 to 5% and most preferably from 0.8 to 2% by weight of the composition.

In order to achieve better blurring effect and/or opacity, the weight ratio of the turbostratic boron nitride to the porous silica is preferably from 20:1 to 1:10, more preferably from 8:1 to 1:2, and even more preferably from 4:1 to 1:1.

The composition preferably comprises a silicone elastomer. The silicone elastomer used in the present invention is preferably powder of silicone elastomer.

It is highly preferred that the silicone elastomer is cross-linked. The silicone elastomer can be obtained from curable organo-polysiloxanes. Examples in this respect are: addition reaction-curing organopolysiloxane compositions which cure under platinum metal catalysis by the addition reaction between SiH-containing diorganopolysiloxane and organopolysiloxane having silicon-bonded vinyl groups; condensation-curing organopolysiloxane compositions which cure in the presence of an organotin compound by a dehydrogenation reaction between hydroxyl terminated diorganopolysiloxane and SiH-containing diorganopolysiloxane; condensation-curing organopolysiloxane compositions which cure in the presence of an organotin compound or a titanate ester, by a condensation reaction between a hydroxyl terminated diorganopolysiloxane and a hydrolyzable organosilane (this condensation reaction is exemplified by dehydration, alcohol-liberating, oxime-liberating, amine-liberating, amide-liberating, carboxyl-liberating, and ketone-liberating reactions); peroxide-curing organopolysiloxane compositions which thermally cure in the presence of an organoperoxide catalyst; and organopolysiloxane compositions which are cured by high-energy radiation, such as by gamma-rays, ultraviolet radiation or electron beams. The silicone elastomer is preferably obtained by addition reaction-curing organopolysiloxane compositions which cure under platinum metal catalysis by the addition reaction between SiH-containing diorganopolysiloxane and organopolysiloxane having silicon-bonded vinyl groups The silicone elastomer may either be an emulsifying or non-emulsifying cross-linked silicone elastomer or a combination thereof but preferably the silicone elastomer is non-emulsifying. The term "non-emulsifying," as used herein, defines cross-linked silicone elastomer from which poly-oxyalkylene units are absent. The term "emulsifying," as used herein, means cross-linked organo-polysiloxane elastomer having at least one poly-oxyalkylene (e.g., poly-oxyethylene or poly-oxypropylene) unit.

Preferred silicone elastomers are organo-polysiloxanes available under the INCI names of dimethicone/vinyl dimethicone crosspolymer, dimethicone crosspolymer and Polysilicone-11. More preferably the silicone elastomer is dimethicone/vinyl dimethicone crosspolymer.

Typically the average diameter of the silicone elastomer is from 0.2 to 50 microns, more preferably from 0.5 to 20 microns, even more preferably from 0.8 to 10 microns, and still even more preferably from 1.5 to 6 microns.

The silicone elastomer is preferably present in amount of 0.5 to 20%, more preferably 1 to 15%, even more preferably from 3 to 12%, still even more preferably from 4.5 to 9 by weight of the composition.

To have a better blurring effect and/or opacity, the weight ratio of silicone elastomer to the porous silica is preferably from 1:1 to 40:1, more preferably from 3:1 to 20:1 and even more preferably from 5:1 to 10:1.

Preferably, the composition additionally comprises a whitening pigment. The whitening pigment are typically particles of high refractive index materials. For example the whitening pigment may have a refractive index of greater than 1.3, more preferably greater than 1.8 and most preferably from 2.0 to 2.7. Examples of such whitening pigment are those comprising bismuth oxy-chloride, boron nitride, barium sulfate, mica, silica, titanium dioxide, zirconium oxide, aluminium oxide, zinc oxide or combinations thereof. More preferred whitening pigment are particles comprising titanium dioxide, zinc oxide, zirconium oxide, mica, iron oxide or a combination thereof. Even more preferred whitening pigment are particles comprising zinc oxide, zirconium oxide, titanium dioxide or a combination thereof as these materials have especially high refractive index. Still even more preferably the whitening pigment is selected from titanium dioxide, zinc oxide or a mixture thereof and Most preferred whitening pigment is titanium dioxide.

The average diameter of whitening pigment is typical from 15 nm to 2 microns, more preferably from 35 nm to 800 nm, even more preferably from 50 nm to 500 nm and still even more preferably from 100 to 300 nm. Diameter of whitening pigment refers to the diameter of particles in an unaggregated state. In the event a well-defined sphere is not generated, diameter means the largest measureable distance on a particle The average diameter may be measured for example by scanning electron microscopy (SEM) or transmission electron microscopy (TEM) by averaging the value of at least one hundred particles.

Preferably the composition comprises whitening pigment in an amount of from 0.001 to 10 wt %, more preferably 0.01 to 6 wt %, more preferably still 0.1 to 3 wt % and most preferably 0.2 to 2 wt %.

The composition preferably additionally comprises one or more organic sunscreens. A wide variety of organic sunscreen is suitable for use in combination with the essential ingredients of this invention. Suitable UV-A/UV-B sunscreen include, 2-hydroxy-4-methoxybenzophenone, octyldimethyl p-aminobenzoic acid, digalloyltrioleate, 2,2-dihydroxy-4-methoxybenzophenone, ethyl-4-(bis(hydroxypropyl)) aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethyl-aminobenzoic acid or aminobenzoate, 2-ethylhexyl-p-dimethyl-amino-benzoate, 2-phenylbenzimidazole-5-sulfonic acid, 2-(p-dimethylaminophenyl)-5-sulfonicbenzoxazoic acid, 2-ethylhexyl-p-methoxycinnamate, butylmethoxydibenzoylmethane, 2-hydroxy-4-methoxybenzophenone, octyldimethyl-p-aminobenzoic acid and mixtures thereof. The most suitable organic sunscreens are 2-ethylhexyl-p-methoxycinnamate, butylmethoxydibenzoylmethane or a mixture thereof.

A safe and effective amount of organic sunscreen may be used in the compositions useful in the subject invention. The composition preferably comprises from 0.1% to 10%, more preferably from 0.1% to 5%, of organic sunscreen.

The composition of the invention preferably comprises a skin lightening agent. Vitamin B3 compounds (including derivatives of vitamin B3) e.g. niacin, nicotinic acid or niacinamide are the preferred skin lightening agent as per the invention, most preferred being niacinamide. Vitamin B3 compounds, when used, are preferably present in an amount in the range of 0.1 to 10%, more preferably 0.2 to 5% by weight of the composition.

Compositions of the present invention will also include a cosmetically acceptable carrier. In some embodiments the carrier will be (or at least comprise) a water and oil emulsion, which in certain embodiments may be water-in-oil emulsion. Preferred emulsions, however, are the oil-in-water variety.

Preferred hydrophobic material for use in the oil phase of such emulsions includes emollients such as fats, oils, fatty alcohols, fatty acids, soaps, silicone oils, synthetic esters and/or hydrocarbons.

Silicones may be divided into the volatile and nonvolatile variety. Volatile silicone oils (if used) are preferably chosen from cyclic (cyclomethicone) or linear polydimethylsiloxanes containing from 3 to 9, preferably from 4 to 5, silicon atoms.

Nonvolatile silicones useful as an emollient material include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5\times10^{-6}$ to $0.1$ m$^2$/s at 25° C. Among the preferred nonvolatile emollients useful in the present compositions are the polydimethyl siloxanes having viscosities from about $1\times10^{-5}$ to about $4\times10^{-4}$ m$^2$/s at 25° C.

Specific examples of non-silicone emollients include stearyl alcohol, glyceryl monoricinoleate, mink oil, cetyl alcohol, isopropyl isostearate, stearic acid, isobutyl palmitate, isocetyl stearate, oleyl alcohol, isopropyl laurate, hexyl laurate, decyl oleate, octadecan-2-ol, isocetyl alcohol, eicosanyl alcohol, behenyl alcohol, cetyl palmitate, silicone oils such as dimethylpolysiloxane, di-n-butyl sebacate, isopropyl myristate, isopropyl palmitate, isopropyl stearate, butyl stearate, polyethylene glycol, triethylene glycol, lanolin, cocoa butter, corn oil, cotton seed oil, olive oil, palm kernel oil, rape seed oil, safflower seed oil, evening primrose oil, soybean oil, sunflower seed oil, avocado oil, sesame seed oil, coconut oil, arachis oil, castor oil, acetylated lanolin alcohols, petroleum jelly, mineral oil, butyl myristate, isostearic acid, palmitic acid, isopropyl linoleate, lauryl lactate, myristyl lactate, decyl oleate, myristyl myristate, and mixtures thereof.

Among the ester emollients are:
a) Alkenyl or alkyl esters of fatty acids having 10 to 20 carbon atoms. Examples thereof include isoarachidyl neopentanoate, isodecyl neopentanoate, isononyl isononanoate, cetyl ricinoleate, oleyl myristate, oleyl stearate, and oleyl oleate;
b) Ether-esters such as fatty acid esters of ethoxylated fatty alcohols;
c) Polyhydric alcohol esters. Butylene glycol, ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl mono-stearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols. Exemplative is pentaerythrityl tetraethylhexanoate;
d) Wax esters such as beeswax, spermaceti wax and tribehenin wax;
e) Sterols esters, of which cholesterol fatty acid esters are examples thereof;
f) Sugar ester of fatty acids such as sucrose polybehenate and sucrose polycottonseedate; or
g) mixtures of two or more of the foregoing (a) to (f).

Of particular use also are the $C_{12-15}$ alkyl benzoate esters sold under the Finsolve brand.

Hydrocarbons which are suitable emollients include petrolatum, mineral oil, $C_{11}$-$C_{13}$ isoparaffins, polyalphaolefins, isohexadecane or a mixture thereof.

Amounts of water in the carrier may, for example, range from 1 to 99%, more preferably from 5 to 90%, even more preferably from 35 to 80%, optimally between 40 and 70% by weight of the personal care composition.

Other materials which can be included in the cosmetically acceptable carrier include solvents, humectants, thickeners and powders. Examples of each of these types of material, which can be used singly or as mixtures, are as follows:

Solvents include ethyl alcohol, isopropanol, acetone, ethylene glycol monoethyl ether, diethylene glycol monobutyl ether, diethylene glycol monoethyl ether and mixtures thereof.

Humectants include those of the polyhydric alcohol-type. Typical polyhydric alcohols include polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, isoprene glycol, 1,2,6-hexanetriol, glycerol, ethoxylated glycerol, propoxylated glycerol and mixtures thereof. The amount of humectant may range, for example, anywhere from 0.5 to 50%, more preferably between 1 and 15% by weight of the composition. Most preferred is glycerol (also known as glycerin). Amounts of glycerin may range, for example, from 0.5% to 50%, more preferably from 1 to 35%, optimally from 2 to 15% by weight of the composition.

A variety of thickening agents may be included in the compositions. Illustrative but not limiting are stearic acid, Acrylamide/Sodium Acryloyldimethyltaurate Copolymer (Aristoflex AVC), Hydroxyethyl Acrylate/Sodium Acryloyldimethyltaurate Copolymer, Aluminum Starch Octenyl Succinate, Polyacrylates (such as Carbomers including Carbopol® 980, Carbopol® 1342, Pemulen TR-2® and the Ultrez® thickeners), Polysaccharides (including xanthan gum, guar gum, pectin, carageenan and sclerotium gums), celluloses (including carboxymethyl cellulose, ethyl cellulose, hydroxyethyl cellulose and methyl hydroxymethyl cellulose), minerals (including talc, silica, alumina, mica and clays, the latter being represented by bentonites, hectorites and attapulgites), magnesium aluminum silicate and mixtures thereof. Amounts of the thickeners may range, for example, from 0.05 to 10%, more preferably from 0.3 to 2% by weight of the composition.

Powders include chalk, talc, Fullers earth, kaolin, starch, gums, colloidal silica sodium polyacrylate, tetraalkyl and/or trialkyl aryl ammonium smectites, chemically modified magnesium aluminium silicate, organically modified montmorillonite clay, hydrated aluminium silicate, fumed silica, carboxyvinyl polymer, sodium carboxymethyl cellulose and ethylene glycol monostearate.

Preferably, the personal care composition has a L&W (line and wrinkle) index of at least −80% and is capable of maintaining the lightness of the skin. More preferably the personal care composition has a L&W index of −70% to 300% and is capable of improving the lightness of the skin by at least 1. Even more preferably, the personal care composition has a L&W index of −45% to 200% and is capable of improving the lightness of the skin by at least 1. The measurements of L&W index and lightness are described in Example 2.

The personal care composition of this invention is preferably a skin care composition. More preferably, the composition is preferably an antiperspirant composition or a face (except eye lids and lips) care composition. The skin care composition refers to a composition suitable for topical application to human skin, including leave-on and wash-off products. Preferably the term encompasses a fluid liquid, and particularly a moisturizer rather than a make-up product. Most preferred are leave-on compositions. The term "leave-on" as used with reference to compositions herein means a composition that is applied to or rubbed on the skin, and left thereon. The term "wash-off" as used with reference to compositions herein means a skin cleanser that is applied to or rubbed on the skin and rinsed off substantially immediately subsequent to application. The term "skin" as used herein includes the skin on the face (except eye lids and lips), neck, chest, abdomen, back, arms, under arms, hands, and legs. Preferably "skin" means includes the skin on the face (except eye lids and lips) and under arms. More preferably means skin on the face other than lips and eyelids.

The composition can be formulated in any known format, more preferred formats being creams or lotions.

Packaging for the composition of this invention can be a jar or tube as well as any other format typically seen for cosmetic, cream, washing and lotion type products. The compositions may be applied topically and preferably 1-4 milligrams of composition is applied per square centimeter of skin.

The composition of the invention preferably delivers a cosmetic benefit to the skin of an individual to which it is topically applied. Examples of cosmetic benefits include reducing the appearance of fine lines, wrinkles, pores and/or blemish spots; evening skin tone, or a combination thereof on the desired skin surface.

The following examples are provided to facilitate an understanding of the invention. The examples are not intended to limit the scope of the claims.

EXAMPLES

| | | Material | | | |
|---|---|---|---|---|---|
| Trade name | INCI name | Supplier | Diameter (microns) | Surface area (m²/g) | Oil Absorption (g/100 g) |
| Softtouch* CC6097 | Boron Nitride (tubostratic type) | MOMENTIVE | 5 | 30 | — |
| RonaFlair® Boroneige® SF-6 | Boron Nitride (graphitic type) | MERCK | 4.5-8.5 | 3.0-7.5 | — |
| MSS-500/3H | Silica (Porous) | KOBO | 3 | 600-800 | 300 |
| MSS-300/3N | Silica (Solid) | KOBO | 5.5 | | 33 |
| DC9509 (63% solid active) | Dimethicone/Vinyl dimethicone Crosspolymer (and) C12-14 Pareth-12 | DOW CORNING | 3 | — | — |
| SA-TR-10 | Titanium dioxide, Aluminum hydroxide and Dimethicone | Miyoshi Kasei, Inc | 0.4 | — | — |

Example 1

This example demonstrated the preparation of skin care compositions.

TABLE 1

| Ingredient (active wt %) | Samples | | | | | |
|---|---|---|---|---|---|---|
| | 1 | A | B | 2 | 3 | C |
| Water | Bal. | Bal. | Bal. | Bal. | Bal. | Bal. |
| Softtouch*CC6097 | 3.00 | 0 | 3.00 | 3.00 | 3.00 | 0 |
| RonaFlair ® Boroneige ® SF-6 | 0 | 3.00 | 0 | 0 | 0 | 0 |
| MSS-500/3H | 1.00 | 1.00 | 0 | 1.00 | 1.00 | 0 |
| MSS-300/3N | 0 | 0 | 1.00 | 0 | 0 | 0 |
| DC9509 | 0 | 0 | 0 | 8.00 | 0 | 8.00 |
| SA-TR-10 | 0 | 0 | 0 | 0 | 0.60 | 0 |
| Tween 20 | 2.00 | 2.00 | 2.00 | 2.00 | 2.00 | 2.00 |
| Glycerin | 2.00 | 2.00 | 2.00 | 2.00 | 2.00 | 2.00 |
| VP/VA copolymer | 2.50 | 2.50 | 2.50 | 2.50 | 2.50 | 2.50 |
| Cyclopentasiloxane (D5) | 12.00 | 12.00 | 12.00 | 12.00 | 12.00 | 12.00 |
| Simulgel EG | 2.00 | 2.00 | 2.00 | 2.00 | 2.00 | 2.00 |
| Preservative | 0.494 | 0.494 | 0.494 | 0.494 | 0.494 | 0.494 |

A series of skin care compositions were formulated as shown in Table 1.

Example 2

This example demonstrated the performance of the personal care compositions of the present invention.

(1). Measurement of the Gloss Degree of the Artificial Skin Before and after the Personal Care Compositions was Applied.

Wrinkled Bio-skin plates (BP-EW1 # BSC, Beaulax Co., Ltd., Tokyo, Japan) made of polyurethane elastomer were used as substrate to mimic the human skin with wrinkles. A dual-polarized image system called SAMBA (Bossa Nova Technologies, USA) was employed to measure the gloss degree of the wrinkled Bio-skin plates by following the method and principle described by Akira Matsubara [Skin translucency: what is it and how is it measured, The International Federation of Societies of Cosmetic Chemists (IF-SCC) Congress 2006, Osaka, Japan]. A software named SAMBA face system (Version 4.3) was equipped for the analysis. The Wrinkled Bio-skin plates were tested against an incident light with exposure time of 80 msec. The operation mode was parallel polarization and crossed polarization modes.

Then, 28 mg of one sample as prepared in Example 1 was applied to and spread by finger cot within the circle with area of 7 cm² for gloss test and wait for 30 minutes to dry naturally. The gloss of the wrinkled Bio skin plates after the samples were applied were measured again using the SAMBA system.

(2). Calculation of L&W Index

The incident light was reflected and scattered by Bio-skin plates. The specular reflected light kept the same polarization as the incident light whereas the scattering light from the volume (diffused light) was un-polarized. The SAMBA camera acquired successively two images corresponding to two states of polarization (parallel and crossed). The parallel image intensity (P) is contributed from both the reflected and scattered light, and the crossed image intensity (C) is contributed from the scattered light only. The parallel image plus the crossed image is equal to the total image delivered by a traditional camera or perceived by human eye.

The gloss degree was calculated by (P−C)/(P+C). The calculation of gloss degree was performed for each pixel. The standard deviation (STD) of gloss degree is a measure of the uniformity of the skin appearance. The higher the STD is, the lower the uniformity is. Herein we defined a L&W (line and wrinkle) index to demonstrate degree of blurring efficacy of the skin care composition. The L&W index was calculated by (STD of gloss degree before applying sample −STD of gloss degree after applying sample)/(STD of gloss degree before applying sample). The higher the L&W index is, the higher is the blurring efficacy of the sample.

(3). Measurement of Color Effect

Bio-skin plate (Color: 20#, ex. BEAULAX, Co. Ltd., Tokyo, Japan) was employed to measure the color. 0.5 g of samples was coated evenly onto Bio-skin plates with area of 250 cm². The coated bio-skin was naturally dried at around 25° C. for 0.5 hours. The L*, a*, and b* of the Bio-skin plate were measured before and after coating of sample by portable spectrophotometer CM2600d (MINOLTA Co. Ltd., Japan) at 6 points. ΔL*, Δa*, Δb* stand for change in whiteness, redness, yellowness after coating of sample compared to prior to coating respectively. The L*, a* and b* of un-coated Bio-skin plate was 64.11, 13.58 and 17.02, respectively.

TABLE 2

| Sample | L&W index | ΔL* | Δa* | Δb* |
|---|---|---|---|---|
| 1 | −60.09% | 2.13 ± 0.23 | −1.47 ± 0.12 | −3.56 ± 0.33 |
| A | −96.76% | 1.57 ± 0.09 | −1.12 ± 0.05 | −2.01 ± 0.08 |
| B | −112.61% | 1.76 ± 0.18 | −1.17 ± 0.12 | −2.93 ± 0.39 |
| 2 | 51.17% | 1.30 ± 0.24 | −0.82 ± 0.13 | −2.01 ± 0.35 |
| 3 | −29.95% | 2.83 ± 0.25 | −1.87 ± 0.17 | −3.90 ± 0.29 |
| C | 18.17% | −0.09 ± 0.30 | 0.15 ± 0.08 | 0.34 ± 0.13 |

Table 2 shows the test results of the L&W index and ΔL*, Δa*, Δb*. It was surprisingly found that the composition of the present invention not only had higher efficacy but also was capable of enhancing the lightness of the skin more than composition containing graphite type boron nitride (Sample 1 vs. Sample A) and composition containing solid silica (Sample 1 vs. Sample B). It was also surprisingly found that silicone elastomer was capable of synergistically boosting the blurring efficacy (Sample 2 vs. Sample 1 and C). Furthermore, the addition of titanium dioxide (Sample 3) was able to improve both the blurring efficacy and lightness of the skin as compared to Sample 1.

The invention claimed is:

1. A personal care composition comprising:
   a) turbostratic boron nitride;
   b) porous silica having a specific surface area of higher than 300 m²/g; and
   c) a cosmetically acceptable carrier;
   wherein oxygen content is from 1 to 3% by mole of the turbostratic boron.

2. The composition as claimed in claim 1 wherein the turbostratic boron nitride has an average diameter from 100 nm to 100 microns.

3. The composition as claimed in claim 1 wherein the turbostratic boron nitride is present in amount of 0.01 to 15% by weight of the composition.

4. The composition as claimed in claim 1 wherein the porous silica is a microsphere having an oil absorption value of higher than 100 g/100 g.

5. The composition as claimed in claim 1 wherein the porous silica has an average diameter of from 200 nm to 40 microns.

6. The composition as claimed in claim 1 wherein the porous silica is present in amount from 0.01 to 20%.

7. The composition as claimed in claim 1 further comprising 1 to 15% silicone elastomer by weight of the composition.

8. The composition as claimed in claim 7 wherein the silicone elastomer is a vinyl dimethicone/dimethicone crosspolymer.

9. The composition as claimed in claim 1 further comprising a whitening pigment having a refractive index higher than 1.8.

10. The composition as claimed in claim 9 wherein the whitening pigment is selected from titanium dioxide, zinc oxide, or a mixture thereof.

11. The composition as claimed in claim 9 wherein the whitening pigment is present from 0.1 to 10% by weight of the composition.

12. The composition as claimed in claim 1 wherein the carrier is an oil-in-water emulsion.

13. The composition as claimed in claim 1 further; comprising an organic sunscreen.

14. The composition of claim 1 wherein the composition reduces the appearance of fine lines, wrinkles, pores and/or blemish spots; evens skin tone, or a combination thereof on a skin surface and the turbostratic boron nitride has an average particle diameter from 1 to 15 microns and makes up from 0.4 to 8% by weight of the composition; the porous silica has a absorption value of higher than 280 g/100 g and an average diameter from 1 to 20 microns and is present in an amount from 0.2 to 9%.

15. A method of reducing an appearance of fine lines, wrinkles, pores and/or blemish spots; evening skin tone, or a combination thereof on skin comprising the step of applying a composition as claimed in claim 1 topically to a skin surface.

* * * * *